(12) United States Patent
Helmick, IV et al.

(10) Patent No.: US 12,379,734 B2
(45) Date of Patent: Aug. 5, 2025

(54) WATER CONTROL SYSTEM FOR CLOSED-LOOP WATER SYSTEMS

(71) Applicant: Universal City Studios LLC, Universal City, CA (US)

(72) Inventors: Nathaniel David Helmick, IV, Winter Park, FL (US); Michael Anthony Beatrice, Orlando, FL (US); Elliot Taylor, Winter Springs, FL (US)

(73) Assignee: Universal City Studios LLC, Universal City, CA (US)

( * ) Notice: Subject to any disclaimer, the term of this patent is extended or adjusted under 35 U.S.C. 154(b) by 483 days.

(21) Appl. No.: 17/714,017

(22) Filed: Apr. 5, 2022

(65) Prior Publication Data

US 2023/0288945 A1    Sep. 14, 2023

Related U.S. Application Data

(60) Provisional application No. 63/319,046, filed on Mar. 11, 2022.

(51) Int. Cl.
| | |
|---|---|
| *G05D 7/06* | (2006.01) |
| *E03B 1/02* | (2006.01) |
| *G01N 33/18* | (2006.01) |
| *G05B 15/02* | (2006.01) |

(52) U.S. Cl.
CPC ............. *G05D 7/0676* (2013.01); *E03B 1/02* (2013.01); *G01N 33/18* (2013.01); *G05B 15/02* (2013.01)

(58) Field of Classification Search
CPC ......... G05D 7/0676; E03B 1/02; G01N 33/18
See application file for complete search history.

(56) References Cited

U.S. PATENT DOCUMENTS

| 6,758,231 | B1 | 7/2004 | Lochtefeld et al. |
| 8,883,079 | B2 | 11/2014 | Clark |
| 10,589,182 | B2 | 3/2020 | Helmick et al. |
| 2003/0203760 | A1 | 10/2003 | Henry et al. |
| 2007/0257806 | A1 | 11/2007 | Madden et al. |
| 2010/0160054 | A1 | 6/2010 | Henry |

(Continued)

FOREIGN PATENT DOCUMENTS

CN        108178436 A      6/2018

OTHER PUBLICATIONS

PCT/US2023/014913 International Search Report and Written Opinion mailed Jun. 13, 2023.

*Primary Examiner* — Mark A Connolly
(74) *Attorney, Agent, or Firm* — Fletcher Yoder, P.C.

(57) ABSTRACT

A water control system includes at least one water effect device configured to use a water source to emit water responsive to a control signal, a plurality of sensors configured to generate water condition data of a closed-loop water source, and a controller having a processor and a memory. The memory may store instructions executable by the processor that cause the controller to receive the water condition data from the plurality of sensors. The controller is also configured to determine whether the water condition data is indicative of a passing water quality or a failing water quality of the closed-loop water source and transmit the control signal to the water effect device to emit water using the closed-loop water source as the water source upon determining that the water condition data is indicative of the passing water quality.

20 Claims, 5 Drawing Sheets

(56) References Cited

U.S. PATENT DOCUMENTS

| | | | |
|---|---|---|---|
| 2013/0212800 A1* | 8/2013 | Kaler | E03B 1/041 |
| | | | 4/597 |
| 2014/0053909 A1* | 2/2014 | Savage | E03B 1/041 |
| | | | 137/563 |
| 2021/0268392 A1 | 9/2021 | Jeromin et al. | |

* cited by examiner

WATER CONTROL SYSTEM FOR CLOSED-LOOP WATER SYSTEMS

CROSS-REFERENCE TO RELATED APPLICATIONS

This application claims priority to U.S. Provisional Application No. 63/319,046 filed Mar. 11, 2022, entitled "WATER CONTROL SYSTEM FOR CLOSED-LOOP WATER SYSTEMS," which is hereby incorporated by reference in its entirety for all purposes.

BACKGROUND

The present disclosure relates generally to the field of amusement parks. Specifically, embodiments of the present disclosure relate to techniques to manage amusement park operations, including monitoring and maintaining closed-loop water sources for amusement park attractions.

Water-based attractions at amusement parks have substantially grown in popularity in recent years. To address this increasing demand, water amusement parks have been expanding by adding new types of water rides, attractions and a variety of water-based effects, including water-based shows, weather effects, and queue effects, for guest entertainment or interaction. Since these water-based effects may come in close proximity to or contact with guests, the effects utilize potable water provided directly from a local municipality, which is both costly and wasteful, or from an isolated water body whose water is maintained locally. For example, potable water may be continuously drawn from the local municipality used to create water-based effects, such as mist or rain effects, to cool guests waiting in a queue. However, the continuous use of potable water is expensive and creation of water-based effects may negatively alter water quality, causing additional challenges for water monitoring.

SUMMARY

Certain embodiments commensurate in scope with the originally claimed subject matter are summarized below. These embodiments are not intended to limit the scope of the disclosure, but rather these embodiments are intended only to provide a brief summary of certain disclosed embodiments. Indeed, the present disclosure may encompass a variety of forms that may be similar to or different from the embodiments set forth below.

In an embodiment, a water control system includes at least one water effect device configured to use a water source to emit water responsive to a control signal, a plurality of sensors configured to generate water condition data of a closed-loop water source, and a controller having a processor and a memory. The memory may store instructions executable by the processor that cause the controller to receive the water condition data from the plurality of sensors. The controller is also configured to determine whether the water condition data is indicative of a passing water quality or a failing water quality of the closed-loop water source and transmit the control signal to the water effect device to emit water using the closed-loop water source as the water source upon determining that the water condition data is indicative of the passing water quality.

In an embodiment, a method includes generating water condition data using a plurality of sensors of a closed-loop water source and determining that a water condition of the closed-loop water source is outside of a pre-determined tolerance based on the water condition data. The method may also transmit instructions to a water effect controller to deactivate water flow from the closed-loop water source to a water effect device and generate updated water condition data using the plurality of sensors. The method may then determine that a water condition of the closed-loop water source is within the pre-determined tolerance based on the updated water condition data and transmitting instructions to the water effect controller to reactivate water flow from the closed-loop water source to the water effect device.

In an embodiment, a fluid effect device includes one or more fluid outlets configured to emit fluid responsive to control signals and a controller comprising a processor and a memory. The memory stores instructions executable by the processor, which are configured to cause the controller to emit fluid from the one or more fluid outlets responsive to receiving a first control signal, wherein the fluid is drawn from a first fluid source and receive fluid source control instructions from a fluid monitoring system. The controller is also configured to switch from the first fluid source to a second source based on the fluid source control instructions and emit fluid from the one or more fluid outlets responsive to receiving a second control signal, wherein the fluid is drawn from the second fluid source.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
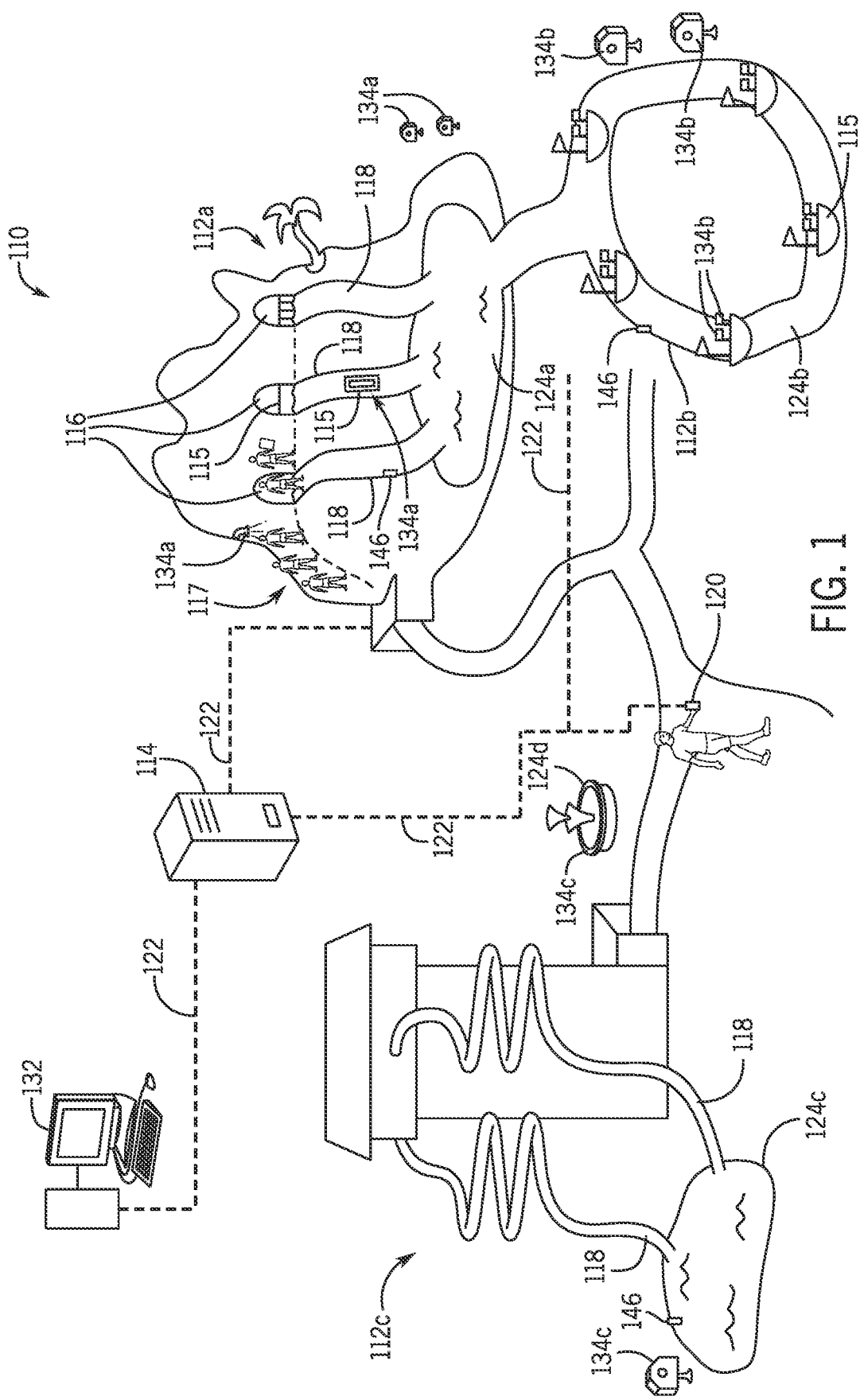
FIG. 1 is a schematic diagram of an embodiment of a theme park including various water effect devices utilizing a water control system, in accordance with present techniques.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

The present disclosure is directed to monitoring and maintaining at least one water condition for a closed-loop water system that creates water-based effects at multiple pickup points for entertaining or interacting with guests. A water amusement park may include a variety of water-based attractions (e.g., water slide rides, kid splash pools) and water effect devices for creating water-based effects, such as devices for weather effects (e.g., rain, fog, steam, mist), water toys (e.g., squirt guns, water blasters, and/or devices for water-based shows (e.g., fountain show). In certain cases, water effect devices may utilize either potable water provided directly from a local municipality, which is both costly and wasteful, or water from a closed-loop water source (e.g., pool, lagoon, fountain, other isolated body of water), which is maintained locally, for creation of water-based effects. Ensuring good water conditions and/or water chemistry is necessary since many water-based effects may come into close proximity to, onto, or possibly even ingested by guests. In order to ensure the safety of persons exposed to the water-based effects, a water control system shall be applied to monitor and ensure that water conditions (e.g., quality) are maintained and exposure to water that falls outside commonly-approved water condition ranges is limited. If quality falls outside of the allowable range, exposure could be automatically limited by removing ability to use or activate the water effect devices for creation of water-based effects.

Provided herein are techniques that monitor water conditions and actively control water effects based on those conditions. For example, passing water conditions may allow water emissions, while a deterioration in water conditions may cause selective deactivation of affected devices, e.g., condition changes may impact a single water effect device while not impacting others or other parts of the theme park. The system may also permit a water effect device to emit water from a secondary water source (e.g., reservoir, tank) in the case of poor water conditions. Additionally or alternatively, the system may switch a mode of operation and permit the water effect device to emit bubbles, light, and/or sound for continuous guest interaction.

It should be noted that although examples provided herein may be presented generally in a water amusement park and water attraction context, such as using the present techniques to facilitate water condition monitoring and control by monitoring various water condition factors of the water amusement park to efficiently provide water to multiple locations, the techniques in this disclosure may be applied to other attractions of an amusement park (e.g., non-water attractions) and non-water related conditions and/or contexts. The non-water attraction and non-water related conditions may include weather effects or effects based on any liquids or fluids (e.g., smoke effects, bubble effects, steam effects, slime effects) that may draw water or liquids from a closed-loop water system.

With the foregoing in mind, FIG. 1 is a schematic representation of a water theme park 110 with at least one water attraction 112 and at least one water effect device 134 that creates water-based effects via a water control system.

The water attraction 112 and the devices 134 may operate as part of a closed-loop system, meaning they receive and return water to a closed-loop water source 124. However, as generally discussed herein, the devices 134 may be capable of using a secondary or different water source in the event of a change in water quality. In an embodiment, the water attraction 112 may include a closed-loop water source 124 whose water quality is monitored and maintained locally by the water control system and may be the primary water source for the devices 134. The closed-loop water source 124 as provided herein may additionally or alternatively be a body of water such as a pond, lagoon, fountain, or aquarium. The water attractions 112a and 112b may include closed-loop water sources 124a and 124b, which may be fluidically connected to form a water supply for the devices 134a and 134b. Further, the device 134c may be connected to the closed-loop water sources 124b and 124c. That is, the device 134c may draw water from or return water to either closed-loop water source. In an embodiment, the water theme park 110 may operate as a singular closed-loop system. In other embodiments, individual attractions 112 or other water features may be implemented as separate water sources 124 and the water theme park 110 may include multiple closed-loop systems. For example, a first closed-loop system may include water attraction 112a with the closed-loop water source 124a, and at least one water effect device 134a. The water attraction 112a may draw water from the closed-loop water source 124a and inject it at the top of the ride to recirculate the water. Further, the devices 134a may pump water from the closed-loop water source 124a for the water-based effects. The devices 134a may also return water back into the closed-loop water source 124a to maintain consistent water levels within the closed-loop system. The water theme park 110 may also have a second closed-loop water system including water attraction 112b, closed-loop water source 124b, and devices 134b, and a third closed-loop system including water attraction 112c, closed-loop water source 124c, and device 134c. As such, poor water conditions within one closed-loop system may not affect the water conditions of another system. Further, water may be diverted from one closed-loop system to another based on the water control system.

Turning back to FIG. 1, certain water attractions 112 may feature a plurality of water slides 118. For example, in the depicted embodiment, a water attraction 112a may include multiple water slides 118 that may be accessed via a single queue 117, which may permit access to a dispatch location 116 for the guests. To provide entertainment to or interaction with the guests, the queue 117 and the dispatch location 116 may include one or more water effect devices 134a that emit water for water-based effects, such as weather effects (e.g., rain, fog, steam, mist), or include water toys (e.g., squirt guns, water blasters). For example, the user (e.g., operator) may flip a switch on the devices 134a to create a weather effect (e.g., mist) to cool guests while they wait in the queue 117. In another example, the users (e.g., guest) may interact with the devices 134a (e.g., water toys) and spray water at each other while in the queue 117 for entertainment. The devices 134a may draw water from the closed-loop water source 124a and the water may be returned as it flows down a side of the water attraction 112a. Additionally or alternatively, the devices 134a may have a secondary water source (e.g., reservoir, tank) located near the dispatch location 116 and/or within the devices 134a that may provide water to the devices 134a, based on instructions from the water control system. Accordingly, the devices 134a may be distributed among the park and the water pick-up point may be dynamic.

Once in the dispatch location 116, the guests may board a ride vehicle 115 to enter the water slides 118 and experience the water attraction 112a. The ride vehicle 115 may include one or more devices 134a for water-based effects and a secondary water source (e.g., reservoir). The devices 134a may draw water from the closed-loop water source 124a for creation of water-based effects. For example, the device 134a may be a squirt gun and the guest may use it to shoot water during the ride. The squirt gun may draw water from the closed-loop water source 124a in response to guest activation. In another example, the ride vehicle 115 may include a reservoir that may draw and store water from the closed-loop water source 124a based on instructions from the water control system. The squirt guns of the ride vehicle 115 may also receive water from the reservoir and emit it in response to guest activation.

Guests not on water attractions 112 may still interact with or be entertained by the water effect devices 134. For example, guests walking by the water attraction 112c may use the devices 134c (e.g., water blasters) to create water-based effects, such as shooting water. The guests observing water attraction 112c may use water blasters to shoot water at other guests, who are on or walking by the attraction 112c. The guest may activate the water blaster by inserting a token, pressing a button, tapping a display, or the like. The water blaster may receive water from the closed-loop water source 124c based on instructions from the water control system. The water blaster may also emit the water in response to the guest activation. In another example, a closed-loop water source 124d may also be a device 134c that recycles water for water-based effects. The closed-loop water source 124d may be a standing body of water, such as fountain, lagoon, or pond, and include a device 134c, such as a jet that may emit water. A park operator may use the devices 134c to create water-based shows for guest entertainment. As such, the device 134 may draw water from the standing body of water based on instructions from the water control system. The device 134c may emit the water, which may return back to the closed-loop water source 124d.

The water control system may include a water monitoring system 114 that monitors one or more water conditions of the closed-loop system and outputs a signal to the water control system. The water monitoring system 114 may include one or more sensors 146 that monitor a condition of the water, such as to water quality (e.g., passing, failing), chemical composition, pH, bacteria of the water in the closed-loop system (e.g., closed-loop water source, secondary water source) to ensure water conditions are within tolerance (e.g., allowable range). For example, the water monitoring system 114 may receive a signal indicative of one or more water conditions of the closed-loop water source 124 and determine if the water conditions are within tolerance. The water monitoring system 114 may output this signal to the water control system. Further, the water monitoring system 114 may receive a signal of water conditions with the secondary water source. In an embodiment, the water control system may receive the signal and cause the devices 134 to automatically switch a water source. The default state of the devices 134 may be to draw water from the closed-loop water source 124 and the water control system may cause the devices 134 to switch to drawing water from the secondary water source, in response to a signal from the water monitoring system 114.

To ensure the safety of guests, the water control system may allow water emissions for effects when the water conditions of the closed-loop system are within tolerance. In certain embodiments, if all or most of the water conditions are within allowable ranges, the water control system may output a signal (e.g., control signal) to activate water flow to and/or from the devices 134. For example, the water control system may allow guests to use the devices 134c to shoot water at other guests in response to the water conditions being within tolerance. In other embodiments, one or more water conditions outside of allowable ranges may cause the water control system to stop water flow and/or switch water sources to actively control water flow. For example, the water control system may switch a mode of the devices 134 to limit exposure to water outside of allowable ranges. The water control system may transmit a signal to the device 134 to change from a water-emitting mode to a different mode that emits bubbles, light, sound, or the like for continuous guest operations. As such, the water control system may remove the ability to use or fire water from the devices 134 by change an operating mode. In another example, the water control system may switch the water source of the devices 134 by stopping water flow from the closed-loop water source 124 and activating water flow from the secondary water source. The water control system may receive a signal indicative of passing water conditions for the secondary water source and output a signal to the devices 134 allowing water emissions.

In one embodiment, the water conditions determined by the water monitoring system 114 may be synced to a system in communication with an operator device 120 (e.g., smart phone, guest wrist band, tablet). The operator device 120 may be used to indicate locations where the water condition is out of tolerance for maintenance purposes. In some embodiments, the water monitoring system 114 may be centralized and contain multiple notifications 122, systems, and/or connections (e.g., wired and/or wireless connections) to other systems in the park 110. In one example, a task notification may be communicated to and from the water monitoring system 114 to indicate one or more devices 134 with water condition out of tolerance to assign as a task for an operator. The notifications may include water condition data provided via signals transmitted from the sensors, the location of the device 134, and/or a time of failure.

In the depicted embodiment, the water monitoring system 114 may be centralized and connected to other parts of the park. When the water monitoring system 114 determines a change in water conditions based on signals from the sensors, the system 114 may send an alert of the changes to a monitoring system 132. The monitoring system 132 may be a user or virtual machine that sends real time water conditions and task notifications to resolve the water conditions outside the pre-determined threshold. For example, an operator may receive the task notification via the operator device 120 and manually stop water flow within the closed-loop system via a stopping mechanism (e.g., button, indication on operator device) to override an activate water flow signal if the operator finds any issues beyond those determined by the water effect controller 114. The monitoring system 132 may also be used to recalibrate the sensors 146 to ensure accurate water condition data. As such, the water control system may monitor water conditions of the closed-loop system to ensure the water meets certain pre-determined thresholds before allowing water emissions. Accordingly, monitoring multiple water conditions of the closed-loop system may be complex and may involve considering various water related and device related conditions.

Figure 2:
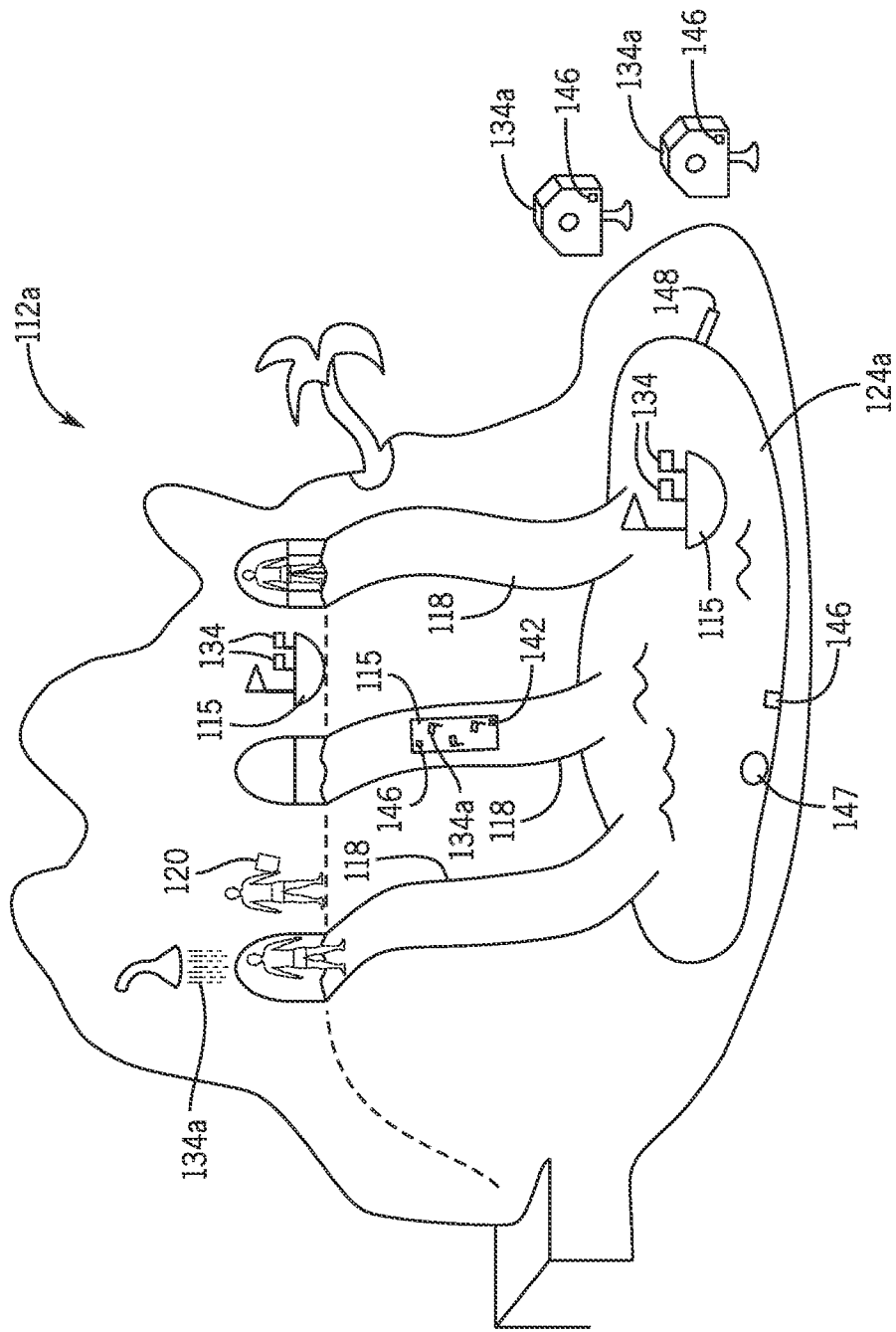
FIG. 2 is a close-up view of an embodiment of the various water effect devices of the theme park utilizing the water control system, in accordance with present techniques.

FIG. 2 illustrates a front perspective view of an example water attraction 112a that may be used in conjunction with the water control system (FIG. 1) to provide instructions for water effect emissions based on a water condition determination from the water monitoring system 114. The depicted embodiment shows various examples of sensors 146 that may be used alone or in combination with one another and in any suitable closed-loop water source. The signal may be sent based on the conditions (e.g., device, water) detected by one or more sensors 146 distributed throughout the closed-loop system (e.g., water attraction 112a, ride vehicle 115, devices 134a, closed-loop water source 124). In an embodiment, the sensors 146 may monitor a device condition, which may be an additional factor for water-based effects. That is, the device 134a may include sensors 146 monitoring one or more device conditions (e.g., part status, blockage, functionality) to determine a functional status of the device. The device 134a may have a broken pump and cannot receive water from the water supply. The sensors 146 of the water blaster may provide a signal indicative of the broken pump and the water control system may stop water flow to and/or from the device 134a. In another embodiment, the sensors 146 may monitor a water condition (e.g., quality), such as water level, pH levels, flow rate, chemical composition, bacterial composition, temperature, etc. For example, the sensors 146 may include a pH sensor that generates pH measurement data. The measurement data may be a pH value from a device 134a or the closed-loop water source 124a. The measured pH value or values may be compared to a pre-set desired pH range. (e.g., about 7.2 to about 7.8). In another example, the sensor 146 may be a chemical composition sensor that monitors the water composition of the closed-loop water source 124a. Depending on the nature of the measured water condition, values falling outside of the pre-set range or greater than or less than a pre-set threshold may be considered to be out of tolerance (e.g., failing). While the illustrated embodiment includes sensors 146 dispersed throughout the closed-loop system, in other embodiments, the sensors 146 may be located in a central location, such as the closed-loop water source 124.

In certain embodiments, based on a determination from the water monitoring system 114 that water conditions are out of tolerance, the water control system may switch to a secondary water source or deactivate water flow. For example, the water control system may cause the devices 134 to draw water from a secondary water source if the water conditions of the closed-loop water source 124a are failing. The devices 134 may include a reservoir that holds an amount of water within tolerance (e.g., passing). As such, the water control system may cause the devices 134 to emit water drawn from the secondary water source. The water control system may also stop water flow by triggering one or more mechanical or electrical effects, such as shutting one or more valves, stopping power from a pump, pinching a hose, or otherwise diverting water flow within the park 110. Further, the water control system may cause the devices 134 to switch a mode of operation to limit exposure to water that is out of tolerance. The devices 134 may operate in one or more alternative modes of operation including a bubble mode, a light mode, a sound mode, or a combination thereof. In certain embodiments, the devices 134 may include a button or a user display that may switch the mode in response to receiving a user input. As a result, the guests may still interact with the devices 134a without creating water-based effects. As such, the devices 134a may remain operational even if the water condition is not within of tolerance. In other embodiments, as noted herein, the result of a water condition outside of pre-set tolerances may result in other outcomes, such as partial or complete closure of the water attraction 112 or the water theme park 110.

The water control system may output a signal indicative of instructions to bring water conditions back into tolerance. Indeed, the water control system may trigger mechanical or electrical effects within the closed-loop system to resolve failing water conditions. For example, the water control system may transmit a signal causing a treatment system 147 to start cleaning the water of the closed-loop water source 124 to bring water conditions back into tolerance. The treatment system 147 may remove particulates and/or chemicals within the water by reverse osmosis, UV sterilization and filtration, heat, and/or chemicals. In this example, operation of treatment system 147 may be dynamic, that is the cleaning may be triggered as-needed based on detection of failing water conditions. The operation of the treatment system 147 may also be periodic (e.g., every hour, every day), which may be set by the operator or the water control system. In another example, the water conditions of the secondary water source may be out of tolerance. For example, the water within a reservoir of the ride vehicle 115 may be out of tolerance and the water control system may output a signal to a pump of the ride vehicle 115 to release the water within the reservoir into the closed-loop water source 124 for filtration. The water control system may also output a signal to the pump indicative of instructions to refill the reservoir with new water to bring water conditions back into an acceptable range. The pump may be configured to periodically initiate refilling based on pre-determined intervals (e.g., after each ride run, once an hour, once a day) set by the operator or the water control system. In certain embodiments, when water conditions may be trending towards out of tolerance, the water control system may cause the pump and/or the treatment system 147 to activate as a safeguard to prevent water conditions from deteriorating. In other embodiments, the operator may use the operator device 120 to provide an indication to the water control system to activate the pump or the treatment system 147.

In certain embodiments, the water control system may indicate to a park operator to resolve failing water conditions. For example, the water control system may indicate to an operator via the operator device 120 used by an operator and/or a light indicator 142 the devices 134 with failing water conditions. For example, the water control system may output a signal to the operator device 120 indicative of a location with failing water conditions (e.g., device 134, closed-loop water source 124). The operator may go to the location to correct the water condition by pressing a button to release water, adding new water within tolerance, start a filtration of the water, or a combination thereof. In another example, the ride vehicle 115 may include a light indicator (e.g., light emitting diode (LED)) that flashes red in response to failing water conditions and green for passing water conditions. The operator may observe the ride vehicle 115 with a red LED and pull the ride vehicle 115 out of the ride to correct failing water conditions. The operator may add water to the reservoir when the ride vehicle 115 reaches the dispatch location 116 via a water injection point.

Figure 3:
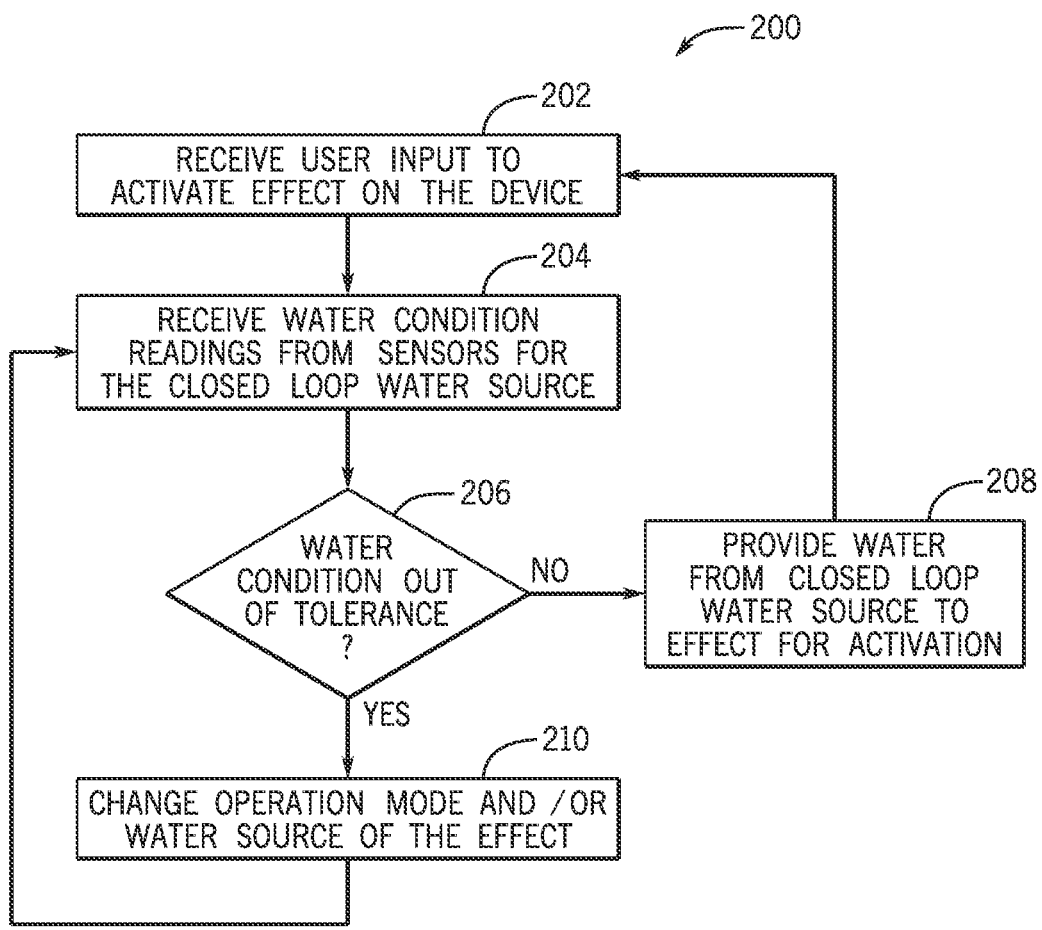
FIG. 3 is a flowchart of an embodiment of a process for operating the water control system of the theme park, in accordance with present techniques.

With the foregoing in mind, FIG. 3 is a process flow diagram 200 of a water monitoring and control technique. The process starts with the water control system receiving (block 202) user input to activate the water-based effect of the devices 134. By way of example, a guest on the ride vehicle 115 may provide user input (e.g., activate) to a squirt gun by pressing a button, lifting the squirt gun from a holder, or tapping a display on the ride vehicle 115. In another example, the guest may want to use a water blaster located near the water attraction 112a. As such the guest may provide input by inserting a coin or pressing a button to activate the water-based effect. Still, an operator may trigger activation of a water-based effect, such as water-based show, by providing an indication to the water control system via an operator tablet 120. The operator may set a periodic activation (e.g., every hour, once a day, once a month) of a weather-based effect, such as rain or mist, for the device 134 located within the park 110. Still in another example, the operator may provide user input by moving a valve, flipping a switch, plugging in a device, or the like, to activate a misting device, a rain device, a fountain, or other water effect devices 134.

Next, the water control system may receive a signal from the plurality of sensors indicative of water condition data of the closed-loop system (block 204). The water conditions may include water level, chemical composition, pH, flow rate, temperature, bacterial composition, or the like. In an embodiment, the plurality of sensors 146 may be located in a central location, such as within the closed-loop water source 124, to ensure that water flowing to the devices 134 may be within pre-determined tolerance. By way of example, the plurality of sensors 146 may include a bacterial composition sensor and a pH sensor located within the closed-loop water source 124 to monitor the bacterial levels and pH values of the closed-loop water source 124. In another embodiment, the plurality of sensors 146 may be distributed throughout the closed-loop system. The plurality of sensors 146 may include a chemical composition sensor, a pH sensor, a temperature sensor, which are located within a reservoir of the ride vehicle 115 to generate multiple water condition points for the secondary water source. Further, the water monitoring system 114 may receive additional water condition data from sensor 146 located on the water attraction 112 to verify the water conditions of the closed-loop system. As such, the water control system may provide redundant and safe monitoring of water within the closed-loop system.

The water monitoring system 114 may determine whether one or more water conditions are out of a pre-determined tolerance (decision block 206). In certain embodiments, the operator may determine thresholds (e.g., upper limit, lower limit) and/or ranges (e.g., deviations) for water conditions. In other embodiments, the water control system may receive a tolerance (e.g., acceptable range) from a database for a respective water condition and calculate this determination by a machine algorithm. The algorithm may analyze the received data (e.g., signal indicative of water condition) and compare it to pre-determined tolerances that may be set by a user or operator. The machine algorithm may also determine a pass or fail water quality based on a pre-determined tolerance for a respective water condition, and then calculate an overall pass or fail based on all water condition tolerances. In one example, the sensors 146 may be a pH sensor that generates pH measurement data. The measurement data may be a pH value from a central location or from multiple locations of the closed-loop system. The measured pH value or values may be compared to a pre-set desired pH range (e.g., about 7.2 to about 7.8). In another example, the water level may be measured by optical sensors to determine if there is sufficient water within the reservoir of the devices 134, within the closed-loop water source 124, or within one or more areas of the water attraction 112. Depending on the nature of the measured water condition, values above, below, or outside of the pre-determined tolerance and/or range may be considered to be out of tolerance.

If the water conditions are or the overall water condition is within tolerance (e.g., passing), the water control system may activate water flow to water-based effects (block 208). The water monitoring system 114 may provide a signal indicative of passing water conditions to the water control system, which may transmit a signal (e.g., control signal) to a pump controller indicative of instructions to activate water flow. For example, the water control system may output a signal to a pump controller of the closed-loop water source 124 indicative of instructions to activate water flow to the devices 134. The water control system may also provide a signal to a pump controller of the devices 134 to emit water for the water-based effect. As such, the devices 134 may create water-based effects with water that is within tolerance. Then, the process 200 may return to receiving the user input (block 202), receiving the water condition reading (block 204), and determining whether the water condition is out of tolerance (determination block 206), as previously discussed. It may be beneficial to redundantly monitor water conditions, because continuous operation of the devices 134 may alter the water conditions of the closed-loop system. That is, the devices 134 may draw water from the closed-loop water source 124, which may cause one or more water conditions to deteriorate. Accordingly, the water control system may continuously monitor and control the flow of water within the closed-loop system.

If the water monitoring system 114 determines one or water conditions to be out of tolerance (e.g., failing), the water control system may limit exposure by stopping water flow (block 210). In one embodiment, a single measured factor being out of tolerance may result in an overall fail determination, regardless of the condition of the other measured factors. For example, the water monitoring system 114 may receive a signal from a chemical sensor within the closed-loop water source 124 indicative of chlorine levels outside of pre-determined thresholds and determine overall failing water conditions for the closed-loop system. The water control system may output a signal to cause the device 134 to change operation mode and/or switch to a secondary water source. In one example, the operation mode is deactivated, and the pump controller blocks water flow. For example, the water control system may output a signal to the pump controller indicative of instructions to stop water flow by closing a valve, stopping power to a motor, pinching a hose, or diverting water flow. Additionally or alternatively, the water control system may switch a mode of the devices 134 to operate in an alternative mode, such as a bubble mode, a light mode, a sound mode, or a combination thereof.

In certain embodiments, the water control system may switch a water source of the devices 134 and allow creation of water-based effects. That is, the devices 134 may be configured to draw water from the closed-loop water source 124 as a default state. The water control system may cause the devices 134 to draw water from the reservoir for water-based effects. The water monitoring system 114 may determine one or more water conditions of the reservoir to be passing and the water control system may transmit a signal to the pump controller of the devices 134 indicative of instructions to create the water-based effects.

The water control system may also output a signal indicative of instructions to resolve the failing water conditions. For example, the water control system may resolve water conditions out of tolerance by outputting a signal to notify an operator of the issue and/or automatically resolve the issue. The water control system may output a signal to the operator tablet indicative of one or more locations with failing water conditions for the operator to resolve. The operator may go to the location to resolve the failing water conditions by adding water, triggering filtration of the water, or switching water sources within the closed-loop system. The operator may also use the operator tablet to indicate to the water control system to trigger filtration of the water, switch water sources, and/or block water flow within the closed-loop system. For example, the water control system may output a signal to a light indicator of the devices 134, which provide a notification to the user of the failing water conditions and/or a mode switch. In another example, the water control system may automatically resolve the failing water conditions by filtering the water or adding new water. The water control system may trigger activation of the reservoir controller to filter or release the water within a reservoir of the devices 134, so that users may not create water-based effects with water out of tolerance. The water control system may also indicate to the pump controller to pump water from a potable water source to dilute the water of the closed-loop system, which may bring water conditions back into tolerance. For example, the water conditions of one or more devices 134 (e.g., water blasters) located near the water attraction 112 may be out of tolerance. The water control system may trigger a reservoir controller to start filtration of water within the reservoir of the devices 134 to resolve out of tolerance water conditions. In another example, the ride vehicle 115 may have a reservoir filled with water out of tolerance. As such, the water control system may signal to the ride vehicle 115 to release the water (e.g., opening a valve) from the reservoir into the closed-loop water source 124. Additionally or alternatively, the water control system may trigger the reservoir controller to start cleaning the water within the reservoir as a way to bring the water conditions back into tolerance. In another example, the water control system may trigger filtration or sterilization of the closed-loop water source 124 in response to returning water by the ride vehicle 115 to ensure water conditions remain in tolerance.

In certain embodiments, the water control system may check whether the water conditions have in fact been brought back into tolerance. This check may be completed by another machine algorithm of the water monitoring system 114 that monitors and detects a change in sensor data. The process 200 may receive new water condition readings from the sensors 146 (block 204) to determine if the failing water condition has been brought within tolerance (determination block 206). If the water conditions have been brought into tolerance, then the process 200 may proceed to provide water to activate the water-based effect (block 208) and return to receive user input (block 202). If the water conditions are out of tolerance and/or trending out of tolerance, then the process 200 may output a signal (block 210) indicative of a notification, trigger one or more mechanical or electrical effects, and/or attempt to resolve failing water conditions. As such, the water control system may monitor water conditions within the closed-loop water source and control water flow to the water effects devices.

The process described above may be stored on one or more tangible, non-transitory, machine-readable media and/or may be performed by the processor of the water control system described above or on another suitable controller. The steps of the process 200 may be performed in the order disclosed above or in any other suitable order. Furthermore, certain steps of the process may be omitted.

Figure 4:
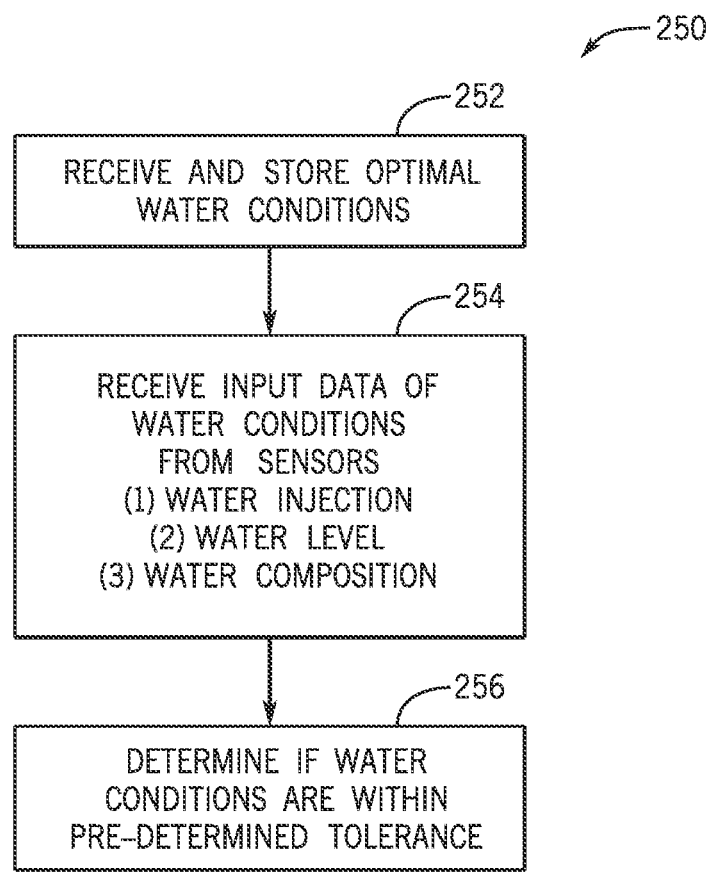
FIG. 4 is a flowchart of an embodiment of a process for operating the water control system of the theme park, in accordance with present techniques.

As illustrated by process 250 of FIG. 4, the water monitoring system 114 considers various water condition factors or inputs for activating water flow. The process may begin with the water control system and/or the water monitoring system 114 receiving (block 252) optimal water condition instructions from a user design, which may be stored in the memory of the water monitoring system 114. The optimal water condition instructions may include pre-determined tolerances for each water condition considered. As previously discussed, a processor-based machine algorithm of the water monitoring system 114 may calculate whether a water condition is, or is trending towards, out of tolerance.

Once the water monitoring system 114 has received and stored the optimal or desired water conditions, it may receive (block 254) sensor data input for multiple water conditions. The water conditions may include, but are not limited to, water injection, water level, water composition, and environmental changes (e.g., weather changes) on or near the water attraction. Each device 134, the closed-loop water source 124, and the water attraction 112 may be associated with respective individual tolerance or states to pass or to be part of an overall water condition status. Certain attraction conditions may be binary. For example, a water condition may be "token input to water blaster?" with "yes" being associated with a passing water condition while "no" is associated with failing. In another example, a water pH level within a desired range is associated with a passing water condition while a pH outside the range is associated with a failing water condition. As provided herein, an overall failing water condition may be triggered when only one or at least one of a plurality of water conditions is outside of tolerance. Conversely, the passing water condition may be associated with all or most conditions being within tolerance or passing. As provided herein, the device 134 may have a default failing water condition as a fail-safe.

In another embodiment, proper water level may be a water condition considered by the water monitoring system 114 when determining water flow for water-based effects. Water level in the device 134 may be considered since it ensures that the reservoir contains enough water to sustain continuous creation of the water-based effect. For example, guests using water blasters may expect a full minute of the water-based effect. If the reservoir does not have enough water to meet expectations, the guest may be disappointed by the experience. The sensors 146 may detect water levels in the reservoir of the device 134 or in the closed-loop water source 124, which may include water levels in the reservoir of the ride vehicle 115, the devices 134, and/or the closed-loop water source 124. The threshold or tolerance for the water level may be set to allow a constant flow of water from the device 134 for creation of the water-based effect.

In yet another embodiment, proper water composition may be a water condition considered by the water monitoring system 114 when determining passing water conditions. Water composition may be considered to ensure chemical balance of the water, which may further ensure minimization of water contamination. The sensors 146 may detect pH level for the closed-loop system, which may include pH levels of water in the devices 134, the closed-loop water source 124, and/or the water attraction 112. Maintaining proper water composition, such as by the pH level and/or chlorine levels, may prevent guest discomfort upon water contact, maintain equipment, and maintain chlorine functionality to prevent contamination. The tolerance for the pH level may be set at 7.2 to 7.8. Another sub-factor that may be used as an indicator for proper water composition may include, but is not limited to, the presence or absence of specific contaminants. Such contaminants may include bacteria, chemicals, particulates, or a combination thereof. The threshold may be set according to a tolerable level of the type and amount of contamination.

Still, in another embodiment, proper water temperatures may be a water condition considered by the water monitoring system 114 when determining water conditions. Water temperature is important to ensure that water emitted from the devices 134 and in contact with guests is not too cold or hot to prevent guest discomfort. The tolerance for water temperature may be set to 75-85° F. The threshold may be changed by the park operator based on the time of day, time of year, or due to weather changes.

After receiving input data for the various attraction conditions, including but not limited to water level, water composition, and water temperature, the processor-based machine algorithm of the water monitoring system 114 may determine (block 256) whether one or more water conditions are out of tolerance. The machine algorithm may implement the determination by comparing the received input data to the pre-set tolerances set by a user and/or stored in a database. Thus, the water monitoring system 114 may monitor and determine whether attraction conditions are within pre-set tolerances before activating water flow for water-based effects.

The process described above may be stored on one or more tangible, non-transitory, machine-readable media and/or may be performed by the processor of the water control system described above or on another suitable controller. The steps of the process 250 may be performed in the order disclosed above or in any other suitable order. Furthermore, certain steps of the process may be omitted.

Figure 5:
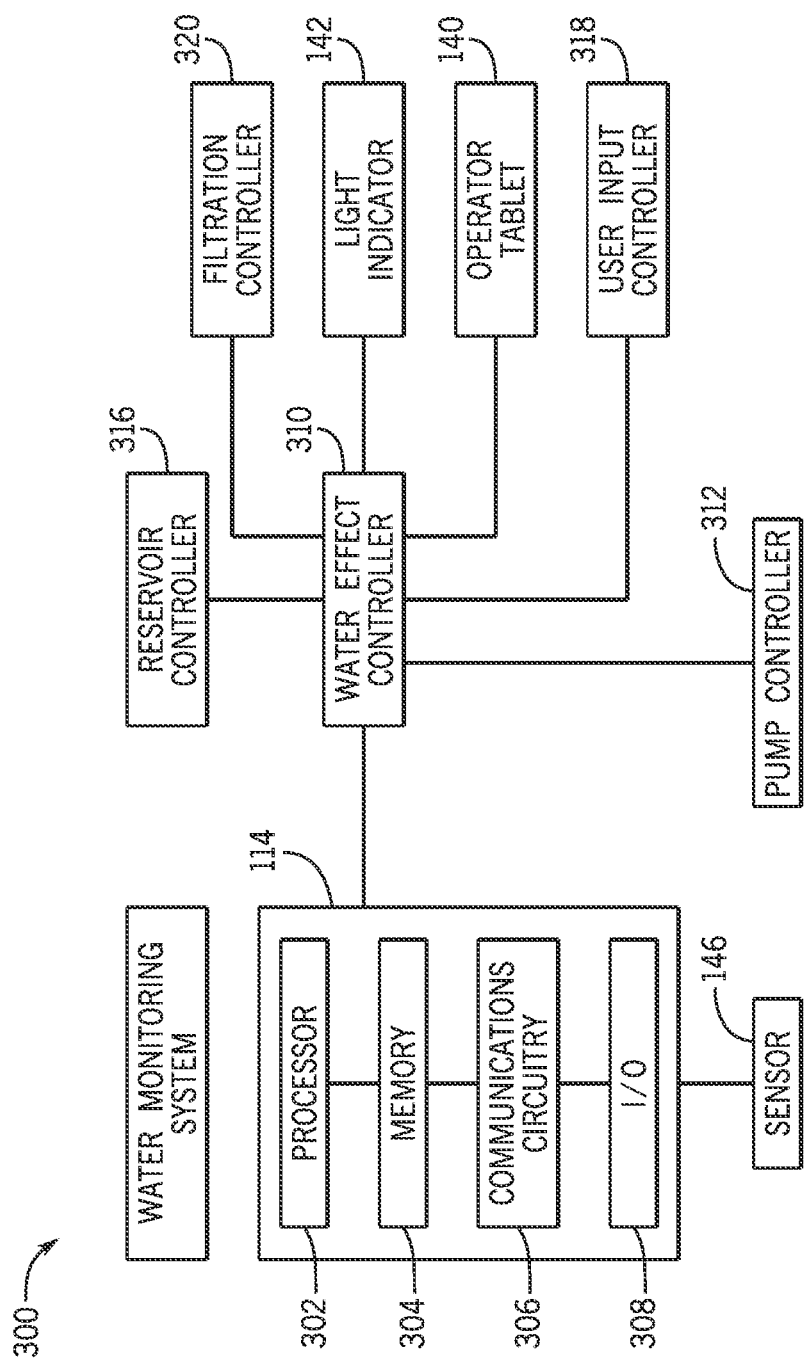
FIG. 5 is a block diagram of an embodiment of the water control system of the theme park, in accordance with present techniques.

FIG. 5 is a block diagram of a water control system 300. The system 300 includes the water monitoring system 114, which may include a memory 304 storing instructions executable by a processor 302 to perform the methods and control actions described herein. The processor 302 may include one or more processing devices, and the memory 304 may include one or more tangible, non-transitory, machine-readable media. By way of example, such machine-readable media can include RAM, ROM, EPROM, EEPROM, or optical disk storage, magnetic disk storage or other magnetic storage devices, or any other medium that can be used to carry or store desired program code in the form of machine-executable instructions or data structures and that can be accessed by the processor 302 or by other processor-based devices (e.g., mobile devices). For example, the water monitoring system 114 may be accessed by an operator interface (e.g., a computer-based workstation or a mobile device, and/or may include an input/output interface 308 and a display). The water monitoring system 114 may include communications circuitry 306, such as antennas, radio transceiver circuits, signal processing hardware and/or software (e.g., hardware or software filters, A/D converters, multiplexer amplifiers), or a combination thereof. The communications circuitry 306 may be configured to communicate over wired or wireless communication paths via IR wireless communication, satellite communication, broadcast radio, microwave radio, Bluetooth, Zigbee, Wifi, UHF, NFC, etc. Such communication may also include intermediate communications devices, such as radio towers, cell towers, etc. While the processor 302, memory 304, communications circuitry 306, and operator interface elements such as the input/output interface have been discussed in the context of the water monitoring system 114, it should be understood that at least some of these hardware components may also be present in other controllers of the system 300.

The water monitoring system 114 is in communication with a water effect controller 310 to provide a signal (e.g., control signal) indicative of one or more water conditions, including a passing or failing determination. Based on data generated by one or more sensors 146, the water monitoring system 114 may assess the water condition to determine an overall water condition. The one or more sensors 146 may include water level sensors, flow rate sensors, pH sensors, temperature sensors, bacterial composition sensors, and/or chemical composition sensors (e.g., oxidative reduction potential sensors indicative of chlorine sterilization activity, free chlorine sensors, combined chlorine sensors) by way of example. In addition, the one or more sensors 146 may include optical sensors that detect a water level within the reservoir of the devices 134 and/or the closed-loop water source 124.

In an embodiment, the water monitoring system 114 may output a signal to the water effect controller 310 indicative of passing water conditions and activate water flow for the water-based effect. The water effect controller 310 may signal to a pump controller 312 to active water flow from the closed-loop water source 124 to the devices 134 to fill the secondary water supply for later use. Additionally or alternatively, the water effect controller 310 may trigger creation of the water-based effects from devices 134 by activating water emissions from the devices 134.

In another embodiment, the water monitoring system 114 may output a signal to the water effect controller 310 indicative of failing water conditions or downward trending water conditions. For example, the water effect controller 310 may output a signal to the operator tablet 140 indicating the locations of failing water conditions with the closed-loop system. The water effect controller 310 may send a signal to the operator tablet 140 indicating a "HOLD" status to notify the operator to prevent people from getting onto the ride vehicle 115 and/or the water attraction 112. The water effect controller 310 may also send a signal to the light indicator 142 to switch from a green LED to a red LED, thus indicating to the user of failing water conditions.

In addition to notifying the operator, the system 300 may also operate to automatically resolve certain failing water condition. The water effect controller 310 may output a signal to the pump controller 312 that may start or stop water flow, a reservoir controller 316 that may release water within the devices 134, a treatment system 147 that may sterilize the water, and/or a user input controller 318 may switch a mode of the devices 134. For example, based on the sensor data, the water effect controller 310 may cause a pump controller 312 to start water flow from a potable water source to the closed-loop water source to bring water conditions into tolerance. That is, adding fresh, potable water that may be within tolerance may dilute the water of the closed-loop water source and change water conditions to achieve measurements within tolerance. The water effect controller 310 may cause the reservoir controller 316 to release the water of the reservoir of the devices 134 for filtration. That is, the reservoir controller 316 may open a valve on the device 134 for water to be released back into the closed-loop water source (e.g., water attraction 112, closed-loop water source 124).

Additionally or alternatively, the reservoir controller 316 may act as a treatment system within the device 134. The water effect controller 310 may activate the treatment system via a filtration controller 320 to start cleaning (e.g., filtering, sterilizing) the water of the closed-loop water source 124. For example, the treatment system may include one or more filters, heat lamps, chemicals, UV lamps, or the like. The treatment system 147 may also include a pump to push water through the system for cleaning. For example, the treatment system 147 may include one or more filters (e.g., that may capture small particles, debris, or germs, within the water source allowing removal or reduction of matter within the water by reverse osmosis, UV sterilization and filtration, heat, and/or chemicals. The treatment system 147 may include one or more filters (e.g., mechanical, adsorptive, neutralizing) that may remove or reduce chemicals, particles, or other matter by catching them before they recirculate back into the water source. In another embodiment, the treatment system 147 may be activated based on water conditions trending towards out of tolerance. As such, the closed-loop water system may be monitored and maintained within the water amusement park 110.

While only certain features of the present disclosure have been illustrated and described herein, many modifications and changes will occur to those skilled in the art. It is, therefore, to be understood that the appended claims are intended to cover all such modifications and changes as fall within the true spirit of the disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A water control system, comprising:
   at least one water effect device configured to use a water source to emit water responsive to a control signal;
   a plurality of sensors configured to generate water condition data of a closed-loop water source; and
   a controller comprising a processor and a memory, wherein the memory stores instructions executable by the processor, the instructions configured to cause the controller to:
      receive the water condition data from the plurality of sensors;
      determine whether the water condition data is indicative of a passing water quality or a failing water quality of the closed-loop water source;
      transmit the control signal to the at least one water effect device to emit water using the closed-loop water source as the water source upon determining that the water condition data is indicative of the passing water quality; and
      transmit the control signal to the water effect device to deactivate water emission when the water condition data is indicative of the failing water quality.

2. The system of claim 1, wherein the water condition data received from the plurality of sensors comprises water level data, water flow data, water composition data, water pH data, environmental changes, weather changes, or a combination thereof.

3. The system of claim 1, wherein the at least one water effect device comprises a reservoir and a pump controller, wherein the pump controller is configured to trigger water flow from the closed-loop water source to the reservoir when the reservoir is low and when the water condition data is indicative of the passing water quality.

4. The system of claim 1, wherein a pump controller of the at least one water effect device is configured to activate a water-based effect based on the control signal.

5. The system of claim 1, wherein a default state of the at least one water effect device is to use the closed-loop water source as the water source.

6. The system of claim 1, wherein the water condition data is indicative of the failing water quality when the water condition data from at least one sensor of the plurality of sensors is out of tolerance.

7. The system of claim 6, wherein the water condition data is out of tolerance based on a measured data value of the water condition data being outside of a predetermined range, above a pre-determined threshold, or below the pre-determined threshold.

8. The system of claim 1, wherein the instructions are configured to cause the controller to trigger activation of a treatment system to filter or sterilize a water of the closed-loop water source upon receiving the water condition data indicative of the failing water quality.

9. The system of claim 1, wherein the instructions are configured to cause the controller to switch an operating mode of the at least one water effect device by switching from a water effect mode to a light effect mode or a sound effect mode.

10. The system of claim 1, wherein the instructions are configured to cause the controller to switch an operating mode of the at least one water effect device upon receiving user input via a display of the at least one water effect device.

11. A method, comprising:
   generating water condition data using a plurality of sensors of a closed-loop water source;
   determining that a water condition of the closed-loop water source is outside of a tolerance based on the water condition data;
   transmitting first instructions to a water effect controller to deactivate water flow from the closed-loop water source to a water effect device;
   transmitting second instructions to the water effect controller to activate water flow from a secondary water source based on the water condition data being outside of the tolerance,
   wherein the secondary water source is a reservoir of the water effect device;
   generating updated water condition data using the plurality of sensors;
   determining that the water condition of the closed-loop water source is within the tolerance based on the updated water condition data; and
   transmitting third instructions to the water effect controller to reactivate water flow from the closed-loop water source to the water effect device.

12. The method of claim 11, comprising:
   transmitting a filtration notification to a treatment system based on the water condition data being outside of the tolerance;
   initiating a filtration or sterilization of the closed-loop water source based on the transmitted filtration notification; and
   generating the updated water condition data using the plurality of sensors of the closed-loop water source subsequent to initiating the filtration or sterilization.

13. The method of claim 11, comprising:
   transmitting a notification to a pump controller based on the water condition data being outside of the tolerance;

initiating an addition of potable water to the closed-loop water source after transmitting the notification to the pump controller; and determining that the water condition of the closed-loop water source is within the tolerance after initiating the addition of the potable water to the closed-loop water source.

14. The method of claim 11, wherein transmitting the second instructions to the water effect controller comprises:
transmitting a notification to a pump controller to provide water to the water effect device from the secondary water source.

15. A fluid effect device, comprising:
one or more fluid outlets configured to emit fluid responsive to control signals; and
a controller comprising a processor and a memory, wherein the memory stores instructions executable by the processor, the instructions configured to cause the controller to:
emit fluid from the one or more fluid outlets responsive to receiving a first control signal, wherein the fluid is drawn from a first fluid source;
receive fluid source control instructions from a fluid monitoring system; and
switch an operating mode of the fluid effect device from a water effect mode to a light effect mode or a sound effect mode upon receiving the fluid source control instructions, wherein the fluid source control instructions are determined upon receiving water condition data indicative of a failing water quality.

16. The system of claim 15, wherein the first fluid source is a closed-loop water source.

17. A system, comprising:
a water effect device configured to use a water source to emit water;
a plurality of sensors configured to generate water condition data of a closed-loop water source; and
a controller comprising a processor and a memory, wherein the memory stores instructions executable by the processor, the instructions configured to cause the controller to:
receive the water condition data from the plurality of sensors;
determine whether the water condition data is indicative of a passing water quality or a failing water quality; and
instruct an operator tablet to display an indication of the failing water quality in response to the determination.

18. The system of claim 17, wherein the indication comprises a location within an amusement park with the failing water quality.

19. The system of claim 17, wherein the instructions are configured to cause the controller to:
transmit a first control signal to the water effect device to emit water using the closed-loop water source as the water source upon determining that the water condition data is indicative of the passing water quality; and
transmit a second control signal to the water effect device to emit water using a secondary water source upon determining that the water condition data is indicative of the failing water quality.

20. The system of claim 17, wherein the instructions are configured to cause the controller to:
receive user input indicative of switching from the water source of the water effect device from a first water source to a secondary water source via the operator tablet; and
transmit a control signal to the water effect device to emit water using the secondary water source upon receiving the user input.

* * * * *